United States Patent
Kerkmann et al.

(10) Patent No.: US 9,904,295 B2
(45) Date of Patent: Feb. 27, 2018

(54) METHOD FOR DEFINING A PROCESS IN A LIQUID HANDLING SYSTEM AND A METHOD FOR CARRYING OUT A PIPETTING PROCESS

(71) Applicant: TECAN Trading AG, Maennedorf (CH)

(72) Inventors: Rainer Kerkmann, Rueti (CH); Pascal Staeheli, Wetzikon (CH); Ho The Vinh, Zurich (CH)

(73) Assignee: TECAN TRADING AG, Mannedorf (CH)

( * ) Notice: Subject to any disclaimer, the term of this patent is extended or adjusted under 35 U.S.C. 154(b) by 296 days.

(21) Appl. No.: 14/710,206

(22) Filed: May 12, 2015

(65) Prior Publication Data
US 2015/0331428 A1     Nov. 19, 2015

(30) Foreign Application Priority Data

May 13, 2014  (EP) .................................... 14168144

(51) Int. Cl.
| | |
|---|---|
| G05D 7/00 | (2006.01) |
| G05D 7/06 | (2006.01) |
| G01N 35/10 | (2006.01) |
| G01N 35/00 | (2006.01) |
| G06F 3/0484 | (2013.01) |
| G05B 19/19 | (2006.01) |
| G05B 19/409 | (2006.01) |

(52) U.S. Cl.
CPC ..... *G05D 7/0623* (2013.01); *G01N 35/00722* (2013.01); *G01N 35/1009* (2013.01); *G01N 35/1011* (2013.01); *G05B 19/19* (2013.01); *G05B 19/409* (2013.01); *G06F 3/04842* (2013.01); *G01N 2035/0091* (2013.01); *G05B 2219/2601* (2013.01); *G05B 2219/40188* (2013.01)

(58) Field of Classification Search
CPC ..................................................... G05D 7/0623
USPC .......................................... 700/282; 422/501
See application file for complete search history.

(56) References Cited

U.S. PATENT DOCUMENTS

| | | | | |
|---|---|---|---|---|
| 4,967,606 A | * | 11/1990 | Wells | .................... B01L 3/0227 422/926 |
| 5,841,959 A | * | 11/1998 | Guiremand | ............ B25J 9/1671 345/440 |
| 6,982,063 B2 | * | 1/2006 | Hamel | ................ G01N 35/028 422/511 |

* cited by examiner

*Primary Examiner* — Mohammad Ali
*Assistant Examiner* — Sheela S Rao
(74) *Attorney, Agent, or Firm* — Notaro, Michalos & Zaccaria, P.C.

(57) ABSTRACT

A method for defining an automated process which is to be carried out in a liquid handling system, wherein the liquid handling system comprises an outlet element (e.g. a pipette) for aspirating and/or dispensing a liquid volume, a numerically controlled movement apparatus for carrying out movements in connection with the aspiration/and or dispensing, and a controller for controlling the process, having the following steps:
  using a graphic user interface in order to enable the user to predetermine parameters which are to be used by the liquid handling system when carrying out one or several substeps of the process,
wherein at least a first parameter is dependent on a second parameter in such a way that the first parameter is adjusted automatically by the system if the second parameter changes.

15 Claims, 11 Drawing Sheets

METHOD FOR DEFINING A PROCESS IN A LIQUID HANDLING SYSTEM AND A METHOD FOR CARRYING OUT A PIPETTING PROCESS

RELATED PATENT APPLICATIONS

This patent application claims priority of the European patent application No. EP 14 168 144.5, filed on May 13, 2014. The whole content of this priority establishing application is herein incorporated by reference in its entirety.

The invention relates to methods for defining an automated process for being carried out in a liquid handling system. In particular, it relates to methods for being carried out in computer-controlled pipetting apparatuses and to carrying out a pipetting process.

BACKGROUND OF THE INVENTION

There are numerous medical, biological, chemical and pharmaceutical devices which involve the handling and use of liquids. Thus, for example, there are automated liquid handling systems for carrying out medical, biological, physical and chemical investigations or to carry out processes in these fields.

Nowadays, most of the automated liquid handling systems are so-called computer-controlled handling systems.

A typical computer-controlled handling system comprises a work area (worktable) for the placement of vessels, a motorized pipetting robot and a controller (usually a processor-based controller). The pipetting robot comprises at least one pipette for aspirating and dispensing liquid samples. Usually, each such pipette is connected by way of flow to a triggerable pump via an individual liquid conduit. The controller is connected by way of circuitry to the pipetting robot and/or the pumps. By implementing a sequential program which is executed in the controller, the pipetting robot can be moved to a specific position in order to execute a specific action there. Thus for example, a pipette can be lowered into a vessel in order to suck up a liquid there or to dispense a liquid.

The individual processes which are carried out in a handling system are mostly subdivided into handling groups. There are the following substeps for example: picking up a pipette, rinsing of a pipette, ejecting a pipette, aspirating, dispensing or mixing a liquid by using a pipette, and the dispensing of a liquid using a pipette.

One example for such a handling system of the present applicant is known on the market under the name of Freedom EVO®.

Such handling systems can be more or less complex. There is a tendency toward quasi standardisation of individual substeps and entire processes in order to better control and perform the individual processes.

The user is guided and supported by a graphic user interface when defining a process. In this connection, this is known as the preparation of a script. Such scripts can be implemented directly by a computer and can be carried out in the handling system, or they can be saved for later use. The substeps of an aspiration process and a dispensing process have mostly been determined in a rigid way as so-called standard actions.

A user interface (graphic user interface, GUI) is known for example from the U.S. Pat. No. 5,841,959, which allows the user to define individual standard actions which are subsequently carried out in a handling system. The user can determine as standard actions for example the aspiration and dispensing as well as the upward and downward movements of a pipette. This is done on the basis of icons which are brought on a screen to the desired chronological sequence. The U.S. Pat. No. 5,841,959 also provides the changing/adjustment of the parameters of individual standard actions.

There is a demand for better handling of repetitive sequences and also for better responding in a flexible way to different sample liquids and reagents and their different physical properties. This is especially relevant in connection with larger test series or examinations.

That is why in modern computer-controlled handling systems so-called liquid classes are used. A liquid class defines the parameters which are to be used on the part of the controller during pipetting of a specific liquid. The word liquid class is a designation which is used here, although other companies use other names for the definition of liquid-specific parameters in a handling system. Current liquid classes are partly subdivided into so-called subclasses. There can be for example a respective subclass for the pipetting volume ranges 3 to 5 µL, 15 to 500 µL, 500 to 1000 µL. Each of these subclasses typically has separate settings. This can lead to the consequence that in the first subclass for example for the range of 3 to 15 µL a different precision correction (a different calibration method) is used than in the next subclass with the range of 15 to 500 µL. In the case of a pipetting volume of 14.9 µL a different correction will be applied than in the case of a pipetting volume of 15.1 µL. This leads to inconsistencies for the precision corrections at the boundaries of the volume ranges.

In one liquid class, the parameters for handling a specific liquid can be defined, e.g. movement velocities of the syringes, accelerations, precision corrections, and/or the parameters for the detection of the liquid level (liquid level detection, LLD), e.g. sensitivity, immersion depth, and/or the parameters of the movements of the pipetting robot such as speeds, accelerations.

For minor adjustments to a liquid class, a given liquid class must be adjusted by the user, which is usually linked to the copying of an existing class, the changing and storing under a different name. This can lead to a confusingly large variety of slightly different liquid classes which are stored in a handling system. Confusion and problems can therefore not be excluded.

Each liquid which is to be used to handling system needs a respective liquid class and parameter in order to ensure the precision and reproducibility of the pipetting of this liquid.

Current handling systems are already supplied with a number of the standard defaults in form of principal liquid classes (e.g. for water, blood serum, ethanol etc) and with standard actions. A liquid class can have numerous parameters (partly more than 30 parameters) which can be adjusted by the user if required. Liquid classes of known handling systems allow a differentiation or selection according to the type of the used pipette such as coated steel cannulas, disposable tips of different volumes, and the pipetting volume to be pipetted. Furthermore, the parameters (such as the aspiration speed) for the aspiration and the parameters (such as the dispensing speed) for the dispensing can be defined within the liquid classes. Often it is possible to provide details on a calibration method which is relevant for the precision of the pipetting process.

Each of the liquid classes thus comprises a number of parameters which are all static, wherein other static parameters are predetermined for a first liquid volume of 3 to 15 µL than for a greater liquid volume 15 to 500 µL for example, as already mentioned above.

The predetermination of the individual parameters is partly very time-consuming, complex and susceptible to errors. There are many correlations and regularities which need to be considered. This concerns among other things the type of liquid, the liquid volume (known as pipetting volume) to be pipetted, the type of pipette, the overall configuration of the handling system and other influencing variables.

In the end, it is necessary that handling systems require a definition of the individual substeps in order to enable precise operation. The definition of the individual substeps however depends on aspects such as the properties of the liquid (viscosity, surface tension, density, vapour pressure), the current hardware configuration, the limits of said hardware, the requirements of the individual process step and ambient influences (pressure, temperature etc).

SUMMARY OF THE INVENTION

It is therefore the object of providing the controller of a handling system in the most flexible and simple manner with the required information so that the virtually infinite number of combinations can be utilised by the user. The solution shall be based on the existing concept of liquid classes and/or standard actions.

In accordance with the invention, a kind of programming level or programming environment (within the meaning of a logical level) is provided which can stand in a programming level above the actual liquid classes or standard actions if liquid classes or standard actions are continued to be used. Depending on the embodiment of the invention, the new programming level or programming environment can also be provided without the use of liquid classes or standard actions.

The additional programming level, which is known here as the microscript level, allows the user to assign parameters and also mechanical actions to a substep and/or a standard action (e.g. an aspiration process) and/or a liquid (e.g. via the use of a liquid class). The scripts of the invention therefore contain further degrees of freedom in comparison with previous standard actions or liquid classes.

In accordance with the invention, the information which was defined within the programming level or programming environment is implemented prior to the execution of a process in a handling system in a suitable sequence of firmware commands (machine commands) which can be processed by the hardware of the handling system. Either the necessary parameters are provided prior to the execution of a process in such a way that they can be processed/interpreted by the existing firmware, or a code is prepared in suitable form which can be processed/interpreted by the hardware of the handling system.

The respective user interface can preferably comprise in all embodiments the typical elements of a modern graphic user interface at the microscript level. Consequently, drag-and-drop actions can be permitted for example in order to define individual parameters at the new microscript level or to define substeps or to bring substeps into chronological reference (process planning or scheduling).

This scheduling preferably occurs in all embodiments with a temporal and spatial reference to the process steps and sequences in the handling system.

The microscript within the terms of the present invention concerns a type of pseudocode which as a result of its structure can be readable for the user. In most computer-controlled handling systems, a script or microscript must be implemented into a kind of machine language (known as firmware) so that the controller of the handling system is capable of controlling the individual motors, pumps and other elements, or the script or microscript must transfer the required parameters to a firmware via an interface so that a computer-controlled handling system can operate.

The method of the invention can be determined in all embodiments in such a way that it has already made a limiting selection on the basis of the currently existing hardware of the handling system when offering menu items, icons, parameters or possibilities for selection at the microscript level. I.e. such a solution consisting of a combination of a controller, a user interface and the hardware of the handling system offers in this preferred case only such menu items, icons, parameters or possibilities for selection at the microscript level which are possible or reasonable in the given constellation. The user can thus preferably only select such microscripts and/or change such parameters which are permitted on the basis of the currently existing hardware.

In all embodiments, the method of the invention can provide the user a possibility to edit, supplement or define individual aspects (e.g. parameters) at the microscript level.

In accordance with the invention, preferably in all embodiments a flexible parameterisation of the liquid classes is concerned. In accordance with the invention, the user can thus preferably determine in all embodiments the parameters and the mechanical steps of a liquid class.

A process is preferably defined in all embodiments step-by-step by chronological successive positioning of substeps at the microscript level. The substeps can be dynamically dependent on each other.

In accordance with the invention, all embodiments beneath a general term defining a process preferably allow stringing substeps together in chronological order, wherein at least one parameter of the respective microscript is not defined as a fixed value but as a function or formula.

In accordance with the invention, preferably in all embodiments a liquid class at the microscript level is no longer a static parameter quantity. Instead, the liquid class comprises at the microscript level several substeps which are combined with each other and which are dynamically dependent on each other (e.g. by using an interlinking function or formula).

In accordance with the invention, preferably in all embodiments several substeps can be combined into a subprocess, wherein said substeps are dynamically linked to each other. The change of one parameter automatically propagates to at least one further substep as a result of the dynamic linking.

In accordance with the invention, preferably in all embodiments the substeps of a microscript are adjusted at the microscript level after a change has occurred in one of the substeps of the microscript. If a parameter of a substep changes for example, all other substeps of this microscript can optionally automatically be adjusted insofar as there is a mutual dependence between these substeps.

In accordance with the invention, one or several of the following substeps can be provided in a predefined form preferably in all embodiments (e.g. by relaying through a graphic user interface):

aspiration of air;
absolute movement;
relative movement;
liquid level detection (LLD);
aspiration of liquid;
monitoring of the aspiration;
dispensing of liquid;
dispensing of air;

mixing of liquids by multiple aspiration and re-dispensing;
picking up and ejecting disposable tips;
washing of pipettes;
etc.

This exemplary list can be expanded in accordance with the invention preferably in all embodiments, which can be useful for example when the existing hardware of the handling system was expanded/supplemented. If a handling system which was previously equipped with a capacitively operating solution for detecting the liquid level is expanded by a pressure-based detection of the liquid level, a substep in form of a microscript for pressure-based detection can be provided/loaded for example (e.g. by relaying through a graphic user interface).

The method in accordance with the invention can be determined in all embodiments in such a way that rigid liquid classes are no longer used. Instead, a standard action is broken down into substeps during the preparation of a microscript.

The method in accordance with the invention can comprise a simulation process in all embodiments. Within the scope of such a simulation process, a standard action and/or its substeps are carried out virtually. This allows the user to perform a plausibility check in combination with respective accompanying display on a screen and to optionally perform adjustments.

The present invention can be used not only in proprietary handling systems but also in open handling systems.

The flexibility of existing and future handling systems can be improved by using the present invention.

The invention is based among other things on the realisation that the current liquid classes will rapidly become confusingly complex due to their flat hierarchical structure. The invention therefore proceeds to provide a deeper hierarchical structure (which is also known as a nested structure) which is more intuitive and simpler.

In accordance with the invention, the entire approach is modular. The parameters of individual substeps can adjust automatically if the same and/or a different parameter was changed in the same and/or a different substep.

The invention relates especially to a method for carrying out analytic and synthetic analysis and other procedures as are performed in so-called liquid handling systems (referred to below as handling systems).

In particular, the invention relates to genetic and/or biochemical and/or chemical and/or physical process steps which are carried out in such handling systems in an automated manner, i.e. by using/control of a controller. The process steps can be in connection with the analysis, synthesis and purification for example.

BRIEF DESCRIPTION OF THE DRAWINGS

The liquid handling systems in accordance with the invention and the methods in accordance with the invention are now explained by reference to schematic drawings of exemplary embodiments, which drawings do not limit the scope of the invention.

DESCRIPTION OF THE PREFERRED EMBODIMENTS

Figure 1:
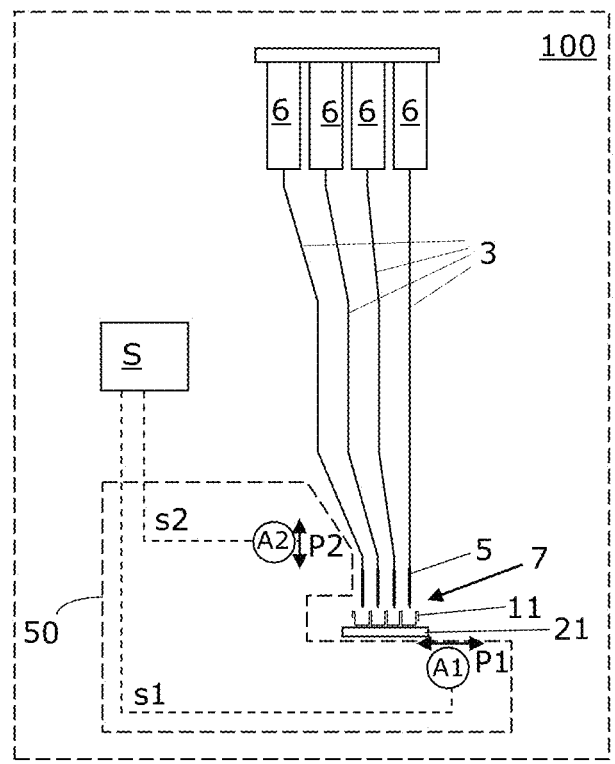
FIG. 1 shows a schematic side view of a first handling system with four channels and a microplate with vessels (wells)

FIG. 1 shows a handling system 100 which is configured as a dispenser and which comprises four parallel channels in this case for discharging liquids. Each channel comprises a conduit 3 which is connected to an outlet element 5. The outlet elements 5 can be arranged in such a way for example that they are spaced from each other at a distance which corresponds to the axial distance of the wells of a microplate 11. The microplate 11 can be arranged in a sample retainer 21 which can be moved (individually or together with a worktable) horizontally in a motorized manner, as indicated in FIG. 1 by the double arrow P1. Alternatively or in addition, the outlet elements 5 can also be moved in a motorized manner, as indicated in FIG. 1 by the double arrow P2. The respective drives are marked here with A1 and A2.

Figure 2:
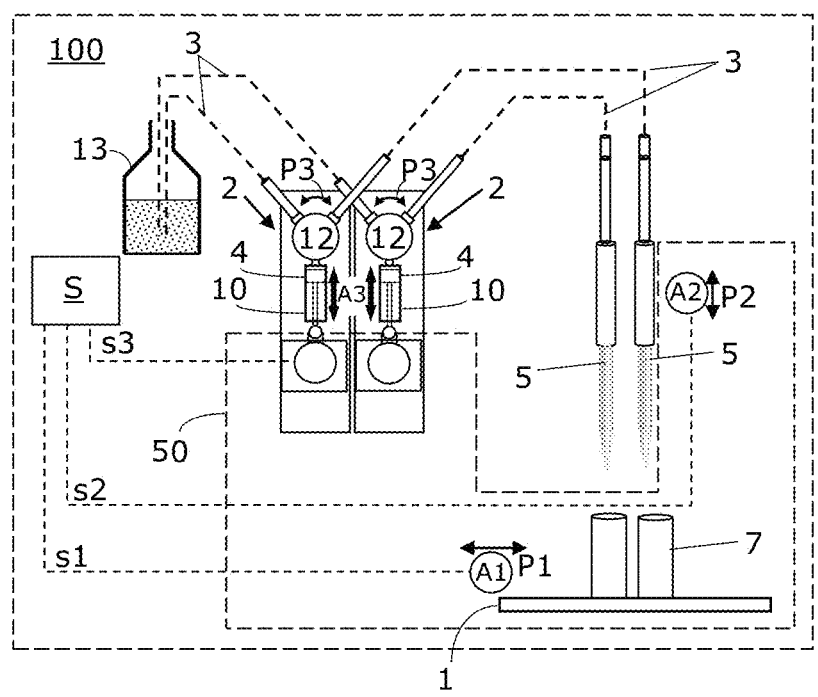
FIG. 2 shows a schematic side view of a further handling system with two channels and two vessels on a worktable.

FIG. 2 shows a further handling system 100 which is configured as a pipettor and which comprises two individual channels for discharging liquids. Each channel comprises one respective conduit 3 which is connected to a pipette 5 at one end. At the other end, one respective syringe pump 2 can be provided per channel. Such a syringe pump 2 comprises in each case a drive A3, which is configured to move a plunger 4 in a syringe cylinder precisely in the upward or downward direction. The movement of the plunger 4 is indicated by the vertical double arrows which are labelled with A3. Each syringe pump 2 further comprises a three-way valve 12, which is configured to either fluidically connect the pipette 5 with the syringe pump 2 for aspiration and dispensing, or to connect the pipette 5 with a system liquid container 13 with system liquid for rinsing the pipettes 5. The rotary movement of the valve 12 is shown in FIG. 2 by the double arrows P3.

The pipettes 5 are arranged in such a way for example that they are spaced from each other at a distance which corresponds to the axial distance of two vessels 7, which can be moved (individually or together with a worktable 1) horizontally in a motorized manner, as indicated in FIG. 2 by the double arrow P1. In addition or alternatively, the pipettes 5 can also be moved in a motorized manner, as indicated in FIG. 2 by the double arrow P2. The respective drives are labelled here with A1 and A2.

The outlet elements 5 may be individual pipettes, tubes, syringes, hollow needles, conduits or the like in all embodiments of the invention. Two or more than two outlet elements 5 can also be combined into groups (e.g. groups of pipettes) in all embodiments.

The handling systems 100 of the invention comprise a respective movement apparatus 50 in all embodiments, as indicated in FIGS. 1 and 2. Notice must be taken that finally relative movements are concerned which are required in connection with the aspiration and/or dispensing. In all embodiments, it is either possible to only move individual outlet elements 5 (or outlet element groups), or only the vessels 7 (e.g. the microplate 11 in FIG. 1 or a worktable 1 in FIG. 2). The movement apparatus 50 of a handling system 100 preferably allows a combination of movements of individual outlet elements 5 (or outlet element groups) and the vessel 7 (e.g. the microplate 11 in FIG. 1 or the worktable 1 in FIG. 2). Details in this connection are adequately known for example from EP0259386.

The movements P1 and/or P2 and/or P3 of such an exemplary handling system 100 are preferably controlled by a controller S, which can also control e.g. the discharge of liquid from the (storage) vessels 6 (as shown in FIG. 1). The control connections between the controller S and the respective drives of the movement apparatus 50 are schematically indicated in FIG. 1 by the control lines s1 and s2 and in FIG. 2 by the control lines s1, s2 and s3.

Such a controller S preferably comprises in all embodiments at least one processor and a respective software (e.g. as a firmware). The controller S can be a part of an external or internal computer 60 (see FIGS. 3 and 4) in all embodiments.

The controller S can also comprise several software and/or hardware modules in all embodiments, wherein one of the modules carries out the handling of the microscripts in accordance with the invention for example. In the end, the cooperation of the controller S and the movement apparatus 50 is provided to trigger in a handling system 100 the execution of individual steps, to perform the steps and to monitor the execution.

In accordance with the invention, the substeps of a microscript at the microscript level are automatically adjusted in preferred embodiments when a change occurs in one of the substeps of the microscript. If a parameter of a substep changes for example, all other substeps of said microscript can be automatically adjusted if necessary, in so far as there is a mutual dependence between at least two substeps. This dynamic link will be explained below by reference to simplified examples.

If a greater liquid volume (known here as the pipetting volume) is to be aspirated within the scope of a process, the controller S can automatically select a suitable larger outlet element 5 in a preferred embodiment which is available in the handling system 100. The selection of a larger outlet element 5 can also occur in all embodiments manually by the user or in a semiautomatic manner.

A larger outlet element 5 (e.g. a pipette) shows a different behaviour during aspiration as a result of the different geometric shape. The substep of aspiration is therefore respectively dynamically adjusted in accordance with the invention. If the movement apparatus 50 is to move the outlet element 5 in an upward direction in a subsequent substep of the process before the outlet element then performs a horizontal movement, the substep of the upward movement must operate with other parameters than in the case of a smaller pipette 5. Put more simply, it may now be necessary to travel with a greater upward lift than before because the larger pipette 5 is longer than the smaller pipette 5. An adjustment of the parameter which defines the upward lift is made automatically in accordance with the invention.

A further simple example is explained below.

A "trailing air gap" (TAG) may be used during pipetting. A trailing air gap can prevent that a liquid inadvertently drips from an outlet element 5. The length of the trailing air gap in the outlet element 5 depends on the size (the volume and/or the geometry) of the outlet element 5. For the purpose of moving the trailing air gap, it is therefore necessary to predetermine respectively different parameters depending on the type of the outlet element. If it is desired to dispense a smaller pipetting volume in a subsequent substep, it is necessary to move the liquid plus the trailing air gap in the direction of the exit of the outlet element with a different movement profile. It is therefore necessary to carry out an adjustment of the parameter which defines the aspiration and/or the dispensing. Preferably, an adjustment of this parameter/these parameters is automatically performed in accordance with the invention in all embodiments. If aspects of the aspiration and/or dispensing are defined as a function of the type of outlet element and/or the volume and/or the geometry, automatic adjustment is carried out.

Preferably, the trailing air gap is defined in all embodiments as a function of the type of the outlet element and/or the volume and/or the geometry.

Figure 3:
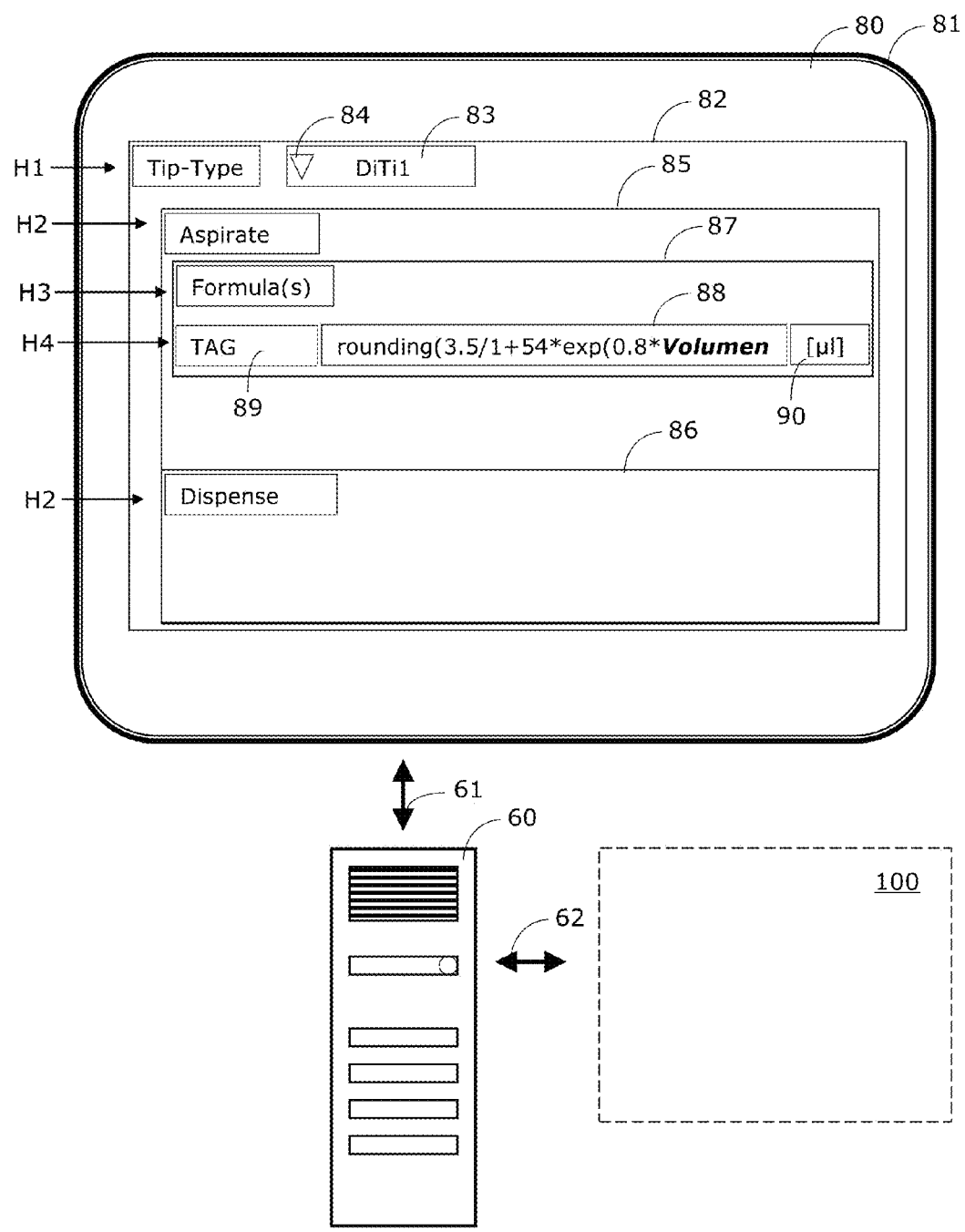
FIG. 3 shows a schematic view of a handling system with a graphic user interface and an external computer according to an embodiment of the invention.

FIG. 3 shows a schematic view of a graphic user interface 80 of an embodiment of the invention, wherein said graphic user interface 80 is connected via a computer 60 to a handling system 100. A computer 60 is designated here as any type of system which comprises at least one processor, a memory and software. The illustration shows the frame of a computer screen 81. Instead of a computer screen 81, other graphic output devices such as touchscreens, smartphones or tablet computers can be used. In the illustrated snapshot, a graphical selection structure 82 is shown. The deep hierarchical structure is chosen in this case as follows. The type of the outlet element can be selected and/or defined in the illustrated example in a first hierarchical level H1. In the illustrated example, an action menu 83 is provided which can be folded out by clicking on the downwardly facing arrow 84 in order to display and select a number of outlet element types. The pipette type DiTi1 is selected in this manner.

The exemplary graphic user interface 80 further shows two hierarchically subordinate menus (designated in this case as submenus 85, 86), which are designated in this case with aspiration and with dispensing. The two submenus 85, 86 are assigned in this case to a second hierarchical level H2.

A formula submenu 87 is provided in the third hierarchical level H3 in the submenu 85. At least one formula field 88 on the fourth hierarchical level H4 can be provided in this case, as shown by way of example in FIG. 3. The formula submenu 87 here shows a formula name 89 for example, followed by the formula field 88 and a mass unit 90. The formula name TAG stands for trailing air gap, which stands for a subsequently trailing air gap, as already mentioned above. The formula field 88 can be a field that can be freely edited by a user, or it can be a field with default values which can be adjusted by the user. In the illustrated example, the trailing air gap is defined as a function in the formula field 88 which depends on the pipetting volume (referred to as volume in the formula field 88). The pipetting volume is a variable quantity here. The pipetting volume may have already been determined in a different process step by the user or the handling system 104 for example, or it can be predetermined by the overall process.

In accordance with the invention, the trailing trailing air gap changes dynamically as a function of the pipetting volume. No adjustments need to be performed here by the user anymore.

The formula submenu 87 can comprise one or several of the following formula fields in all embodiments for the aspiration:

TAG formula field 88 (trailing air gap; the air gap trailing the sample), and/or
LAG formula field (leading air gap; the air gap preceding the sample), and/or
STAG formula field (system trailing air gap; the air gap trailing the system liquid), and/or
excess volume formula field, and/or
conditioning volume formula field, and/or
pipetting speed formula field, and/or
delay formula field, and/or
accuracy adjustment formula field.

These formula fields, or their functions which are indicated within said formula fields, respectively, preferably have a dependence on the pipetting volume (e.g. as shown in FIG. 3) and/or on the outlet element type in all embodiments.

Figure 4:
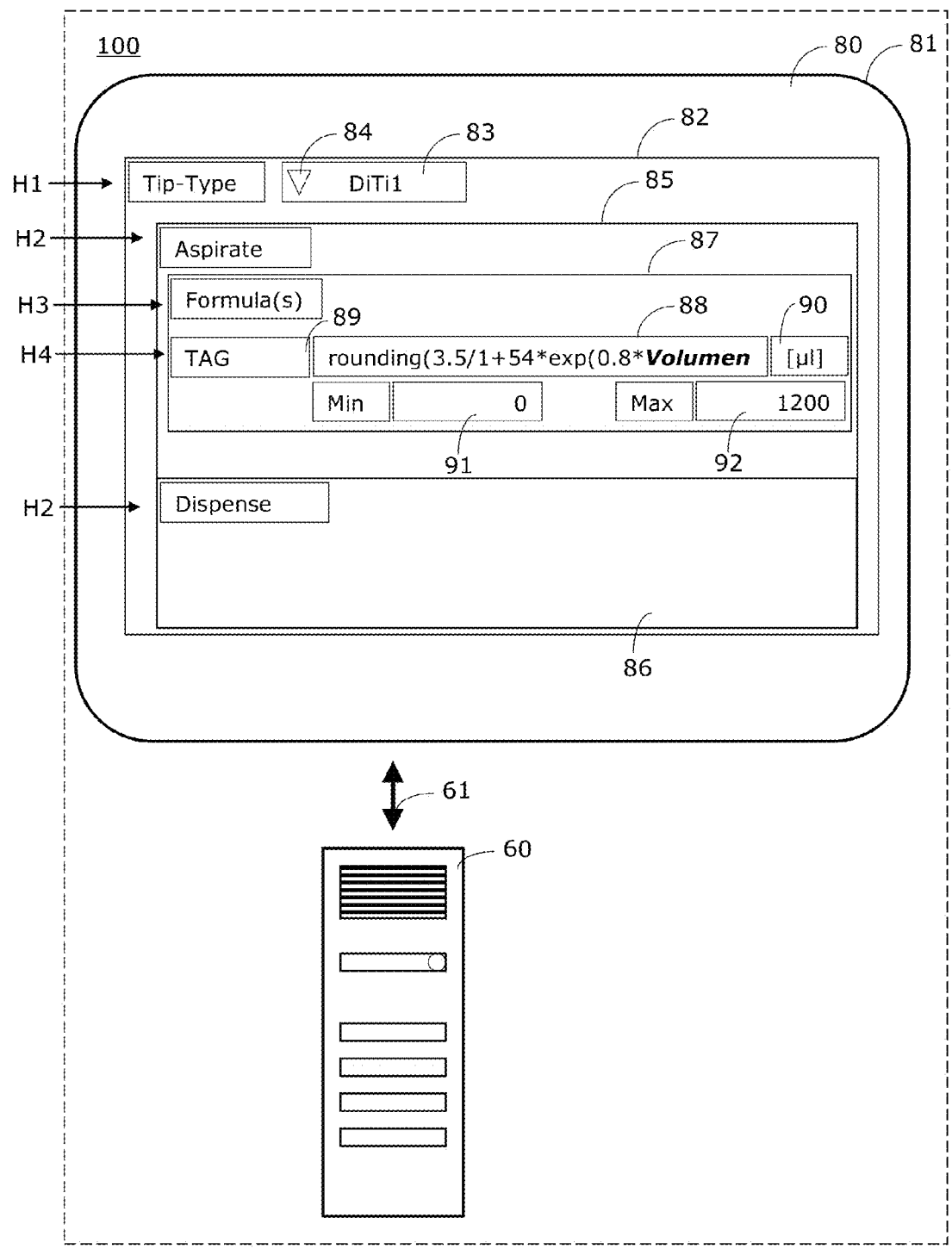
FIG. 4 shows a schematic view of a handling system with a graphic user interface and a computer according to an embodiment of the invention.

A minimum and a maximum value can preferably be entered in all embodiments with respect to at least one of the formula fields, as shown for example in FIG. 4. Minimum and maximum values were assigned in the example in FIG. 4 to the formula field 88. It was thus defined in the illustrated example that the formula of the formula field 88 shall have validity in the range of 0 to 1200 μL. In all other respects, the embodiment of FIG. 4 only differs from the embodiment of FIG. 3 in the aspect that a computer 60 is a part of the handling system 100. The computer 60 is connected via an internal interface 61 to the screen 81. Reference is hereby made to the description of FIG. 3 concerning all other details.

Figure 5:
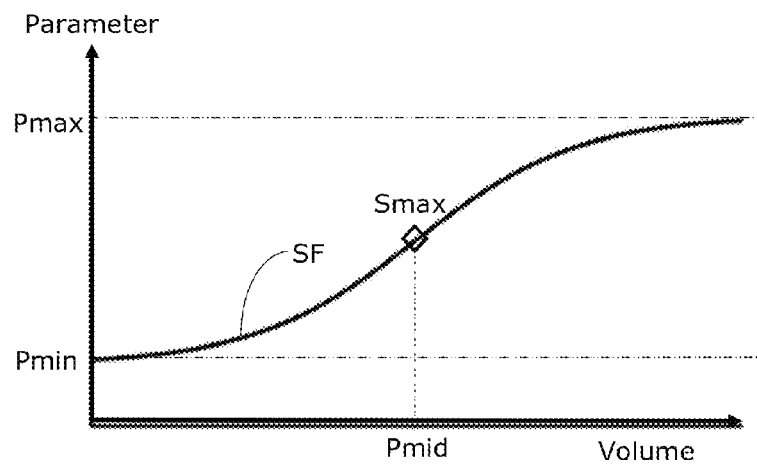
FIG. 5 shows a schematic view of a sigmoid function.

A sigmoid function SF is preferably offered in all embodiments, or a sigmoid function SF can be entered in one of the formula fields. A sigmoid function SF is a non-linear function with S-shaped curve progression, as shown in FIG. 5 by reference to an exemplary graph. The sigmoid function SF is especially suitable for the definition of movement sequences and/or movement contexts due to its special progression, because it helps to prevent abrupt leaps or changes.

The sigmoid function SF can be illustrated as follows, wherein x stands for the pipetting volume and f(x) for the parameter which is dependent on x. e is the Euler's number, and a, b, c and d are constants.

$$f(x) = \frac{a}{1+be^{cx}} + d$$

The sigmoid function SF comprises two horizontal asymptotes Pmax and Pmin, as shown in FIG. 5. If the volume x goes to infinity at a constant c<0, the sigmoid function SF reaches the asymptote Pmax. The following applies:

$$P\text{max}=a+d$$

If the volume x goes to minus infinity at a constant c<0, the sigmoid function SF reaches the asymptote Pmin. The following applies:

$$P\text{min}=d$$

Furthermore, the sigmoid function SF has a point of inflection Smax. The inclination is greatest at this point of inflection Smax. The following applies:

$$S\text{max} = -\frac{ac}{4}$$

The respective pipetting volume at the point of inflection Smax is designated with Pmid.

Departing from FIG. 5, the point of inflection can lie anywhere between Pmin and Pmax instead of in the middle between Pmin and Pmax.

The context between one of the parameters (e.g. the parameter which defines the size of the trailing air gap) and the pipetting volume is preferably defined by a sigmoid function SF in all embodiments in at least one of the formula fields, as shown in FIG. 5.

As a result, the aspiration speed can be defined by a sigmoid function SF according to one embodiment of the invention for example, in that the minimum speed is provided in μL/s, the maximum speed in μL/s, the pipetting volume where the change in the speed shall be greatest in μL, and the maximum change in speed in 1/s. The constants a, b, c and d can be determined therefrom and thus define the sigmoid function SF in the respective formula field.

In accordance with the invention, all affected substeps are adjusted dynamically if a relevant change is made in one of the substeps. If the pipetting volume x should change in one of the substeps, the size of the trading air gap adjusts automatically for example, as predetermined in the formula field 88 in FIGS. 3 and 4.

In accordance with the invention, it is distinguished between a method for defining a sequence of automated process steps (e.g. in a microscript) and the actual implementation or performance of the process steps.

The adjustments on the basis of the dependence of the individual substeps among each other are preferably carried out in all embodiments either during the definition of the sequence (i.e. during compiling the microscript) or after the termination of the definition of the sequence (i.e. after compiling the microscript). This means the individual substeps are defined at first and a function is predetermined at least at one point before subsequently the respective adjustments are (automatically) calculated by taking the function into account.

The adjustments as a result of the dependence of the individual substeps among each other however can also occur in all embodiments during the implementation or during the performance (i.e. during the runtime) of the process steps.

In accordance with the invention, the following method for defining a sequence of automated process steps (e.g. in a microscript) is used. This sequence of automated process steps is carried out by using/under the control of the controller S after the definition of the sequence in a handling system 100. The definition of the sequence of automated process steps can be carried out within the handling system 100 (e.g. by using or by cooperation of the controller S), or it may be carried out by means of a different system, e.g. by means of a (separate) computer 60 which comprises a screen 81 with a graphic (user) interface 80, as indicated in FIG. 3 on the basis of an example. A (separate) computer 60 can be connected via an interface 61 to the screen 81 and via an interface 62 to the handling system 100. It is also possible in all embodiments that the computer 60 plus the screen 81 is a part of the handling system 100, as indicated in FIG. 4. The controller S can be integrated in the computer 60 for example in the embodiment of FIG. 4.

The handling system 100 comprises in all embodiments at least one outlet element 5 which is configured for aspirating and/or dispensing a pipetting volume x of a liquid Fl. An example in this connection is shown in FIGS. 11A to 11F.

The handling system 100 comprises in all embodiments a numerically controlled movement apparatus 54 for carrying out relative and/or absolute movements, which are provided in FIGS. 1 and 2 with double arrows P1, P2, P3. They concern movements P1, P2, P3 which are required in connection with aspirations and/or dispensing. For example, the group of outlet elements 5 can be moved jointly in the downward direction towards the microplate 11 in FIG. 1.

The handling system 100 comprises in all embodiments a controller S which e.g. can be part of a computer 60 and which is configured for controlling the process steps.

The method preferably comprises the following steps in all embodiments:

Use of a graphic user interface 80 (see FIG. 3, 4 or 6 for example) in order to define substeps of the process steps. The user interface 80 is preferably configured in such a way that it allows the user
- to make (directly or indirectly) the selection of an outlet element 5 (selection of a type of outlet element);
- to (directly or indirectly) predetermine (liquid handling) parameters which are to be applied by the handling system 100 when performing one or several of the substeps.

The process is defined in such a way that at least one first parameter f(x) is dependent on a second parameter x (e.g. the pipetting volume) in such a way that the first parameter f(x) is adjusted automatically by the system if the second parameter x changes. A respective example is shown in FIGS. 3 and 4. The trailing air gap (TAG) is defined in the formula field 88 by a function f(x) which depends on the pipetting volume x.

Figure 6:
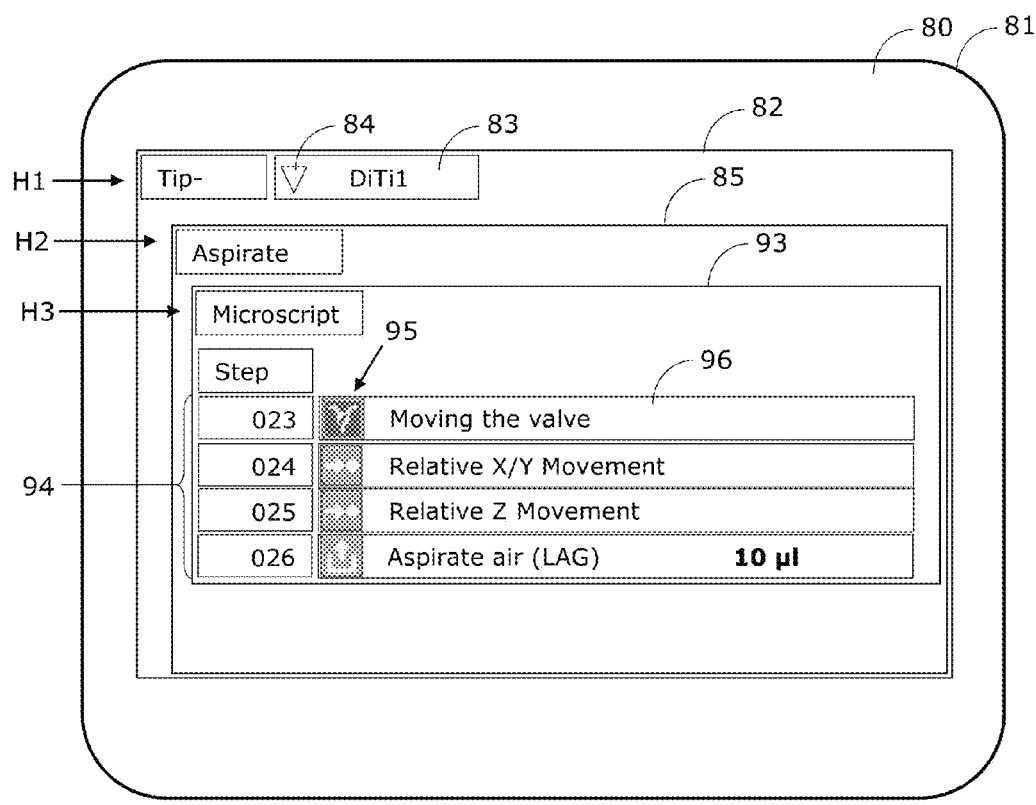
FIG. 6 shows a schematic view of a graphic user interface of a further embodiment of the invention.

The method of the invention preferably comprises in all embodiments a step which allows the user (directly or indirectly) to bring the substeps of the standard action to a chronological sequence with respect each other, as shown by way of example in FIG. 6. The predetermination of a chronological sequence preferably occurs by means of the graphic user interface 80 and by means of input means (keyboard and/or mouse and/or touchscreen 81) of the controller S and/or a computer 60.

FIG. 6 shows an example of the graphic user interface 80 of a screen 81, which is suitable for predetermining the chronological sequence of the substeps. In a submenu 85, which is used for defining the aspiration, the respective means can be displayed in a submenu 93 (e.g. in the hierarchical level H3). The submenu 93 is provided with the title microscript because the predetermination of the chronological sequence is called here microscripting. A microscript can be defined by inputs in the submenu 93, or an existing microscript can be edited.

The graphic user interface 80 preferably shows a column in which the substeps are named or numbered. A step sequence 94 is shown in the illustrated example. In the illustrated snapshot, the steps 023 to 026 are shown. Each substep can comprise a field 96 which comprises a graphic symbol 95 (icon) and/or a descriptive text.

The substeps can preferably be predetermined or changed in all embodiments by drag-and-drop actions.

Details of the individual substeps can preferably be defined in all embodiments. This may be done in such a way for example that the user reaches a respective menu by selecting a substep (e.g. by double clicking). A formula submenu (e.g. in analogy to the formula submenu 87 of FIGS. 3 and 4) can thus be provided for example as a menu. The details of a movement sequence can be stated in such a formula submenu for example.

In step 025 of the example of FIG. 6, it can be defined by means of a formula for example that the speed of the Z movement (lifting movement of the outlet element 5) out of the liquid is adjusted to the immersion depth beneath the liquid level detected by means of LLD and the viscosity of the sample. It is also defined in the step that the pipette is moved upwardly to a sufficient extent so that it is no longer immersed in the sample liquid at step 026.

The process steps of a process can be defined simply and rapidly by using the microscripts. The described method is highly flexible and intuitive.

The parameters and/or functions are preferably determined or prepared from the microscripts in all embodiments.

Figure 7:
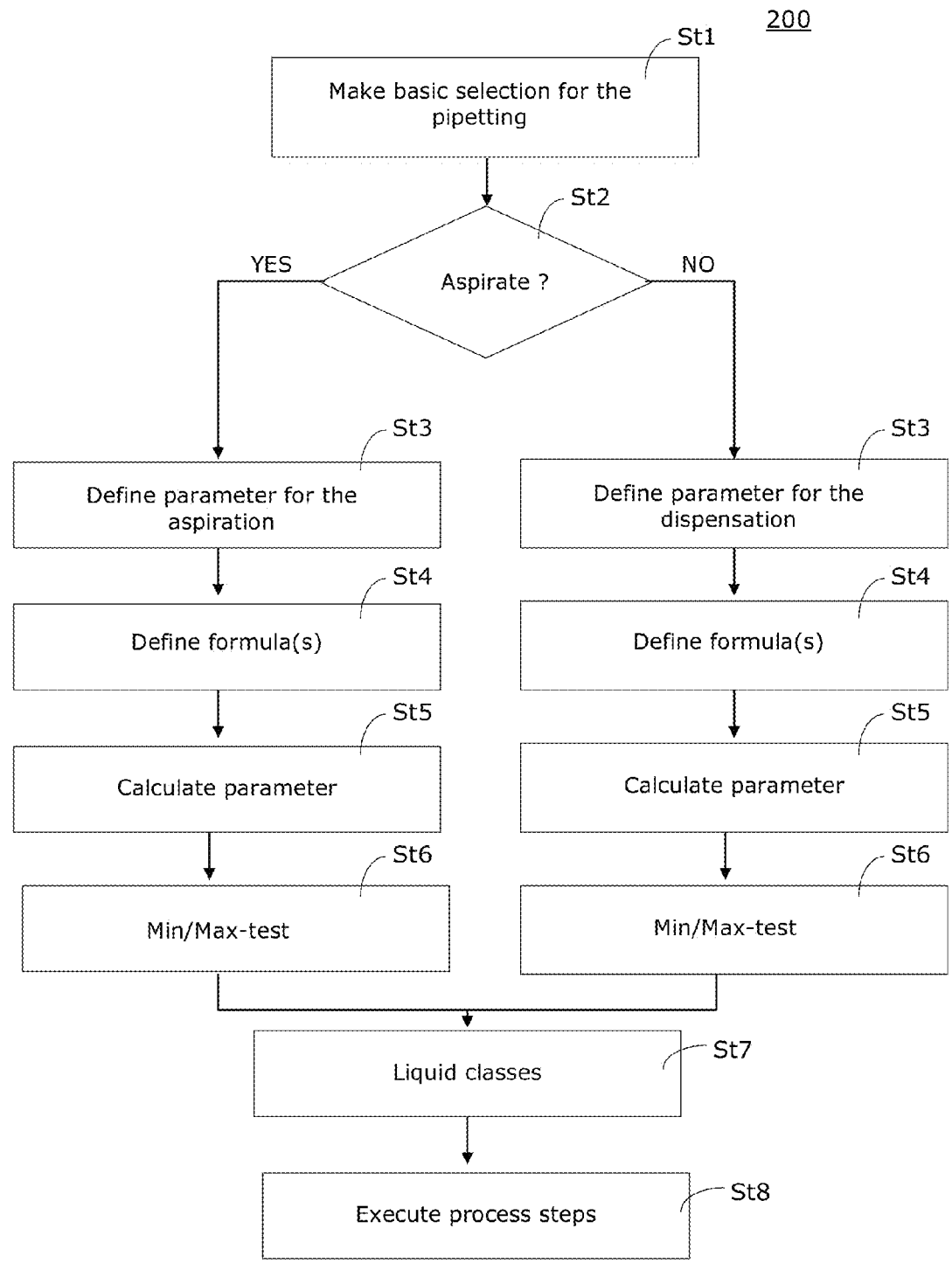
FIG. 7 shows a flowchart of an embodiment of a method of the invention.

FIG. 7 shows a flowchart of an embodiment of a process 200 in accordance with the invention. The individual steps of the process 200 are designated here by reference numerals St1, St2, St3 etc.

In a first step St1, the fundamental details of a process can be defined for example. A basic selection by using a graphic user interface 80 can be made for example. As is shown in FIGS. 3 and 4, the pipette type DiTi1 was selected in this case within the scope of basic selection in both cases, as indicated in field 83.

A selection can be made in a second step St2 for example whether an aspiration process or a dispensing process is to be defined. The selection of an aspiration submenu 85 or a dispensing submenu 86 is therefore enabled at the hierarchical level H2 in the embodiments of FIGS. 3 and 4.

Either the parameters of the aspiration process or the dispensing process can be defined in the step St3. In the step St3, the relevant parameters can be defined by the user or loaded from a memory. Step St3 is optional.

At least one formula can be defined in the step St4. In the step St4, the formula can be defined by the user or loaded from a memory. A respective formula field 88 is provided in the embodiments of FIGS. 3 and 4 in order to define a formula or to edit an existing formula.

The final parameters are calculated in the step St5 which are to be used in the implementation or execution of the process steps.

A minimum check and a maximum check can be performed in the step St6. A respective minimum field 91 and a maximum field 92 are provided for this purpose in the embodiment of FIG. 4. The step St6 is optional.

The determined final parameters can be entered into the grid of a liquid class in step St7. The step St7 is optional and is preferably used when the underlying handling system 100 is configured for processing liquid classes. In these cases, the method in accordance with the invention can be applied to an existing handling system 100. The method of the invention is downward compatible if it comprises the step St7.

The substeps of the aspiration process or the dispensing process in a handling system 100 are carried out in the step St8.

In the process 200 of FIG. 7, the steps St4, St5 and St6 belong to the dynamic part, i.e. there may be mutual dependencies between these steps St4, St5 and St6. Changes may occur by using at least one formula, which changes are carried out automatically by the handling system 100 and/or a computer 60. The parameters are then finally defined before the execution of the substeps (step St8) of the aspiration process or the dispensing process, and do not change any more in this embodiment.

Figure 8:
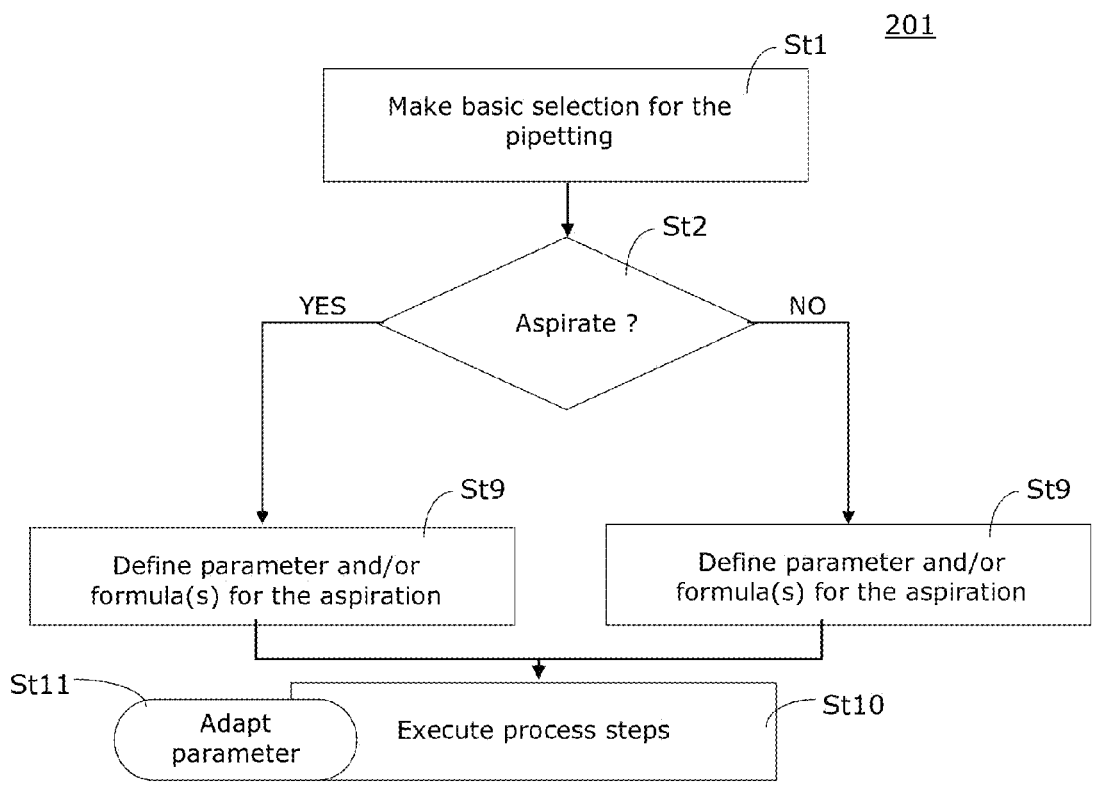
FIG. 8 shows a flowchart of an embodiment of a further method of the invention.

FIG. 8 shows a flowchart of an embodiment of a further process 201 of the invention. The individual steps of the process 201 are designated with the reference numerals St1, St2, St3 etc. The steps St1 and St2 are the same as or similar to those in FIG. 7.

In the step St9 (similar to step St3), either the parameters and/or the formulas of an aspiration process or a dispensing process can be defined. In the step St9, the parameters or formulas can be defined by the user or loaded from a memory. In each case, at least one formula is predetermined in the step St9.

In the step St10 (similar to step St8), the substeps of the aspiration process or dispensing process are carried out in the handling system 100. However, a kind of dynamic adjustment occurs in this case during the execution of the substeps, as indicated in FIG. 8 by the step St11, which is logically linked to the step St10 or is in interaction with the step St10, respectively. The dynamic adjustment occurs during the runtime.

In a process 201 according to FIG. 8, the final parameters are preferably only stored in the main memory shortly before executing a substep. The parameters can still be adjusted until the moment of storage. As a result, such a process and a handling system 100 in which this process is implemented can respond to changing conditions. If there is no sufficient volume of a liquid present in a container 6 for example (see FIG. 1), the pipetting volume which is used in a subsequent substep can be reduced (the reduction occurs according to specifically predetermined rules and notice must be taken that there are substeps in which the adjustment of the pipetting volume is not permissible because it would lead to errors). The reduction in the volume can consequently have an influence on other parameters which are dependent on the volume. Such adjustments can occur quasi in real time or virtually in real time.

Figure 9:
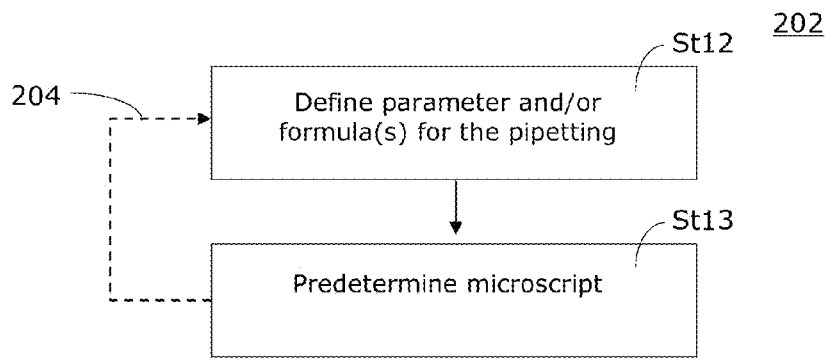
FIG. 9 shows a flowchart of an embodiment of a further method of the invention.

FIG. 9 shows a flowchart of an embodiment of a further process 202 of the invention. FIG. 9 indicates that the microscript-based process is carried out temporally after the definition of the parameters and/or formulas of pipetting. Once all parameters and/or formulas were predetermined in a step St12, the microscript-based process can apply the parameters and formulas in step St13. If the aspiration of air is defined in a step 026 for example in order to produce a leading air gap (LAG) in a pipette 5 (as shown in FIG. 6), the parameters can be applied in the definition of the aspiration of air which were previously defined in step St12.

The respective parameters are preferably displayed on the graphic user interface 80 during the execution of the microscript-based process in step St13. If a leading air gap (LAG) was defined with a parameter of 10 µL in the step St12 for example, then this parameter value can be displayed in the field 96 of FIG. 6. This is shown in FIG. 6 by way of example in field 96 of the step 026.

Changes which can have an influence on other parameters or substeps may occur under certain circumstances during the definition of the substeps by applying the microscript-based process (e.g. in step St13). All embodiments are therefore preferably implemented in such a way that there is a kind of computational feedback 204, as schematically indicated in FIG. 9. The feedback 204 is optional.

Figure 10:
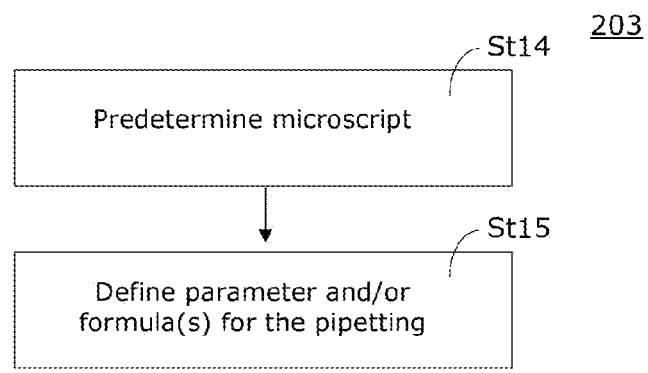
FIG. 10 shows a flowchart of an embodiment of a further method of the invention.

FIG. 10 shows a flowchart of an embodiment of a further process 202 of the invention. FIG. 10 indicates that the definition of the parameters and/or formulas of the pipetting is carried out temporally after the microscript-based process. Once the microscript-based process was applied in a step St14, the parameters and formulas can be predetermined or adjusted in the step St15. Feedback 204 is not necessary in this case.

FIGS. 11A to 11F show exemplary steps of a process which are carried out in a handling system 100 of the invention. The graphic user interface 80 of a screen 81 is shown by way of example on the left side in these illustrations. A respective pipette 5 and a vessel 7 which is filled with a liquid Fl is shown to the right adjacent to the screen 81 in a schematic illustration.

The graphic user interface 80 can show an illustration in all embodiments which represents the progress of the process step-by-step.

The graphic user interface 80 can show in all embodiments a microscript window 93 which is arranged similarly to the microscript window 93 in FIG. 6. The step-by-step illustration of the progress of the process can occur in another form in all embodiments.

Figure 11A:
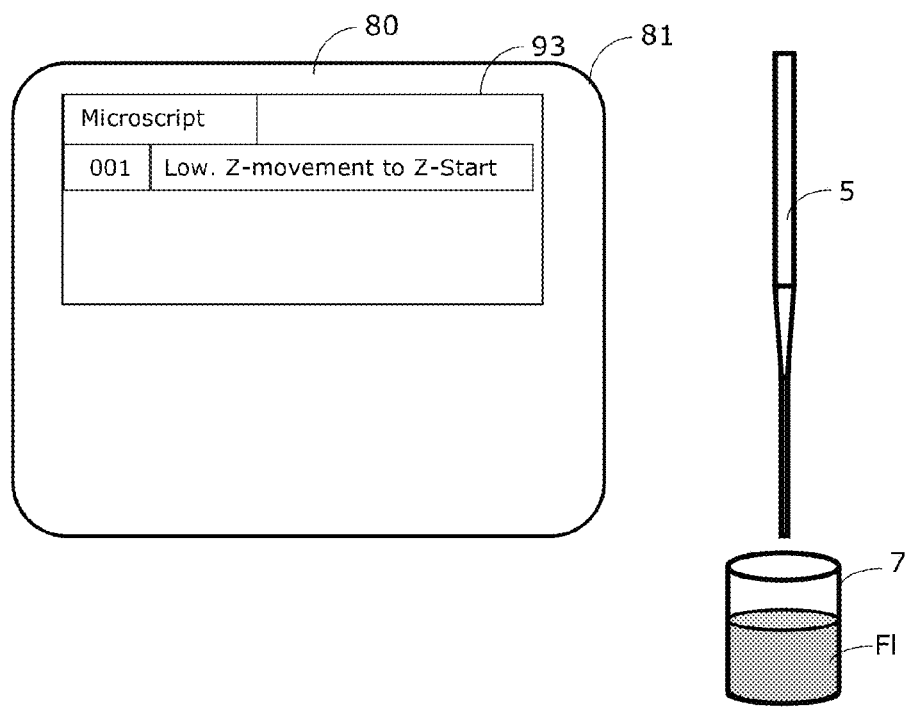
FIG. 11A shows a view of a graphic user interface of the invention during a first aspiration step and a pipette above a vessel on the right side thereof.

FIG. 11A shows the graphic user interface 80 during a first aspiration step. The pipette 5 is situated above the vessel 7. During the first aspiration step, the pipette 5 is brought to a position relative to the vessel 7 by the movement apparatus 50 which is designated with Z-start. From the Z-start on, the pipette 5 is moved downwardly in a substantially slower manner than during the purely robotic movements in X, Y and Z.

Figure 11B:
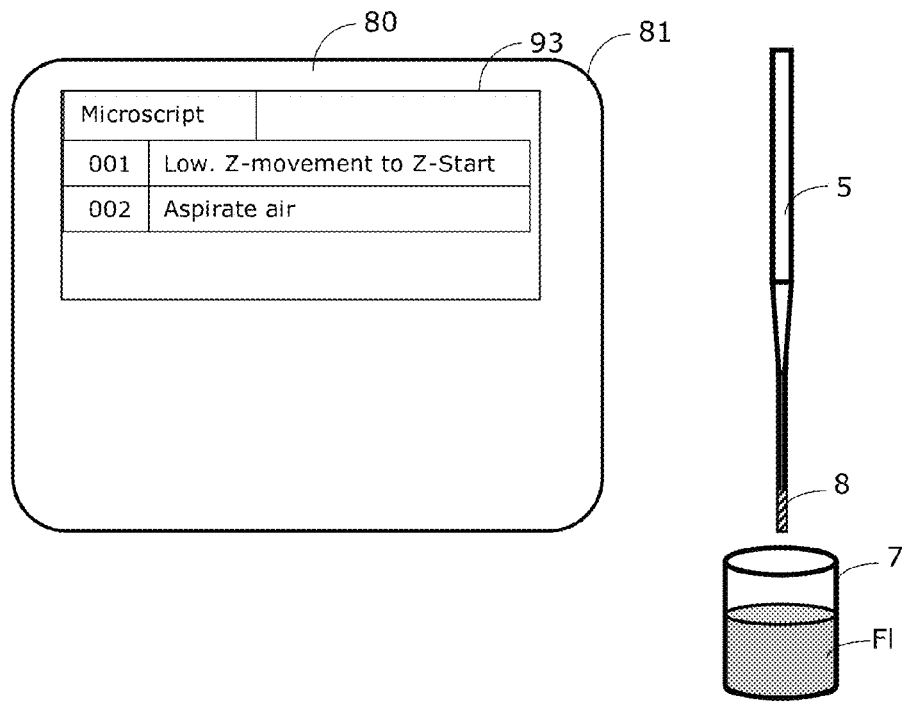
FIG. 11B shows a view of the graphic user interface of FIG. 11A during a second aspiration step and the pipette during the aspiration of air.

FIG. 11B shows the graphic user interface 80 during a second aspiration step. Air was aspirated from the pipette 5 in this step. FIG. 11B shows a small air gap 8 consisting of STAG and LAG at the bottom end of the pipette 5.

Figure 11C:
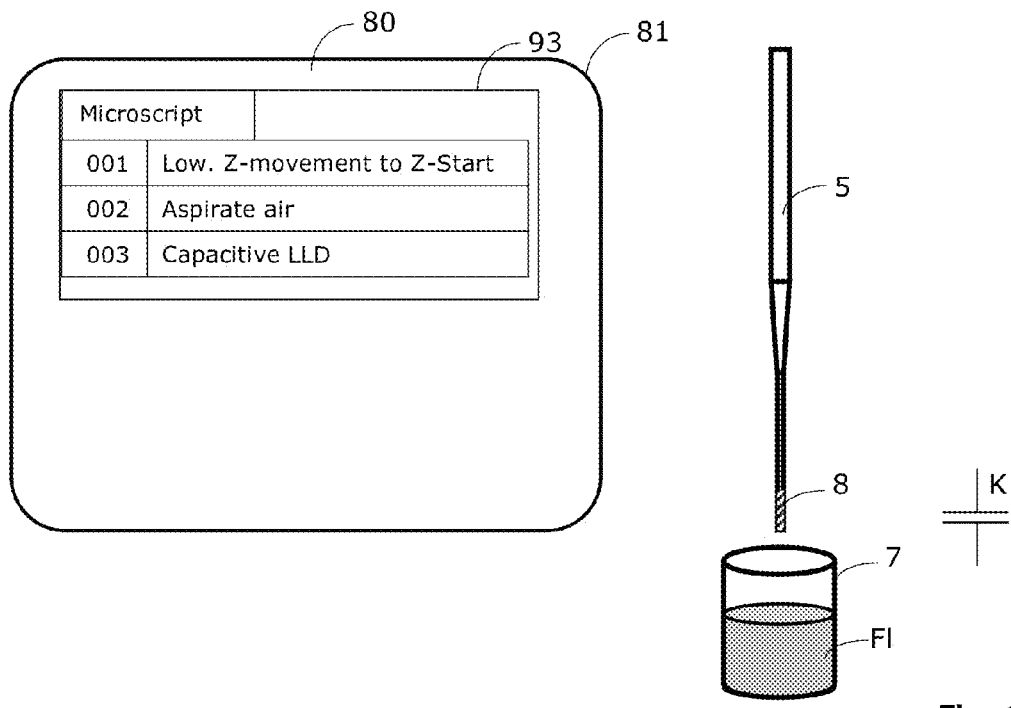
FIG. 11C shows a view of the graphic user interface of FIG. 11A during a third aspiration step and the pipette which is prepared for the capacitive detection of the liquid level in the vessel.

FIG. 11C shows the graphic user interface 80 during a third aspiration step. In order to enable capacitive detection of the liquid level in the vessel 7, a respective LLD circuit (symbolised by the capacitor K) was activated. Details of an exemplary LLD circuit are provided in the published European patent application EP2270445. LLD stands for liquid-level detection, which means the detection of a liquid level. The pipette 5 is subsequently slowly moved from Z-start in the direction of the surface of the liquid.

Figure 11D:
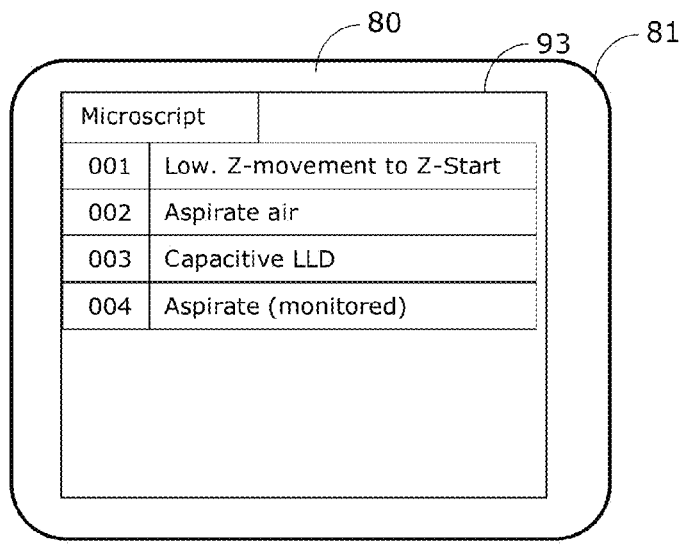
FIG. 11D shows a view of the graphic user interface of FIG. 11A during a fourth aspiration step during the LLD-monitored aspiration of liquid from the vessel.
Figure 11D:
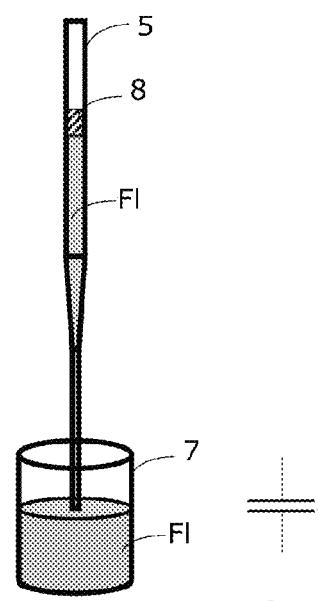

FIG. 11D shows the graphic user interface 80 during a fourth aspiration step. In this step, liquid Fl is aspirated from the vessel 7 by the pipette 5. The pipette 5 is moved downwardly by the movement apparatus 50 during the aspiration in order to thus follow the sinking liquid level in the vessel 7. The aspiration occurs with capacitive LLD monitoring. This means that if the pipette 5 would follow the sinking liquid level during the aspiration too slowly, the LLD circuit would emit an alarm.

Figure 11E:
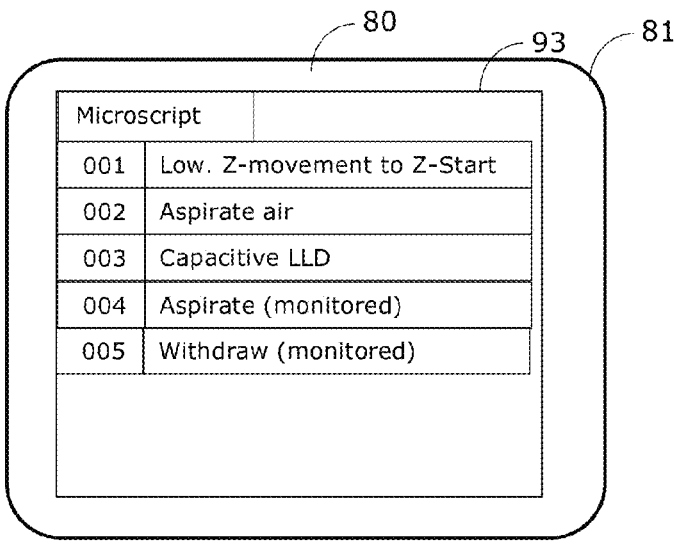
FIG. 11E shows a view of the graphic user interface of FIG. 11A during a fifth aspiration step during the LLD-monitored withdrawal of the pipette from the vessel.
Figure 11E:
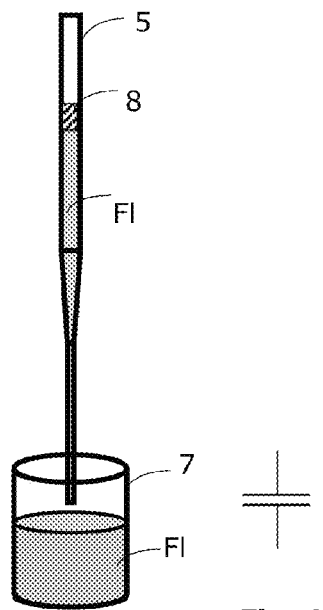

FIG. 11E shows the graphic user interface 80 during a fifth aspiration step. In this step, an LLD-monitored retraction of the pipette 5 from the vessel 7 is carried out. A signal which is monitored by the LLD circuit (symbolised by the capacitor K) indicates once the pipette 5 has emerged from the liquid Fl. The liquid level after the aspiration is subjected to a plausibility check on the basis of the aspirated volume and the vessel geometry.

Figure 11F:
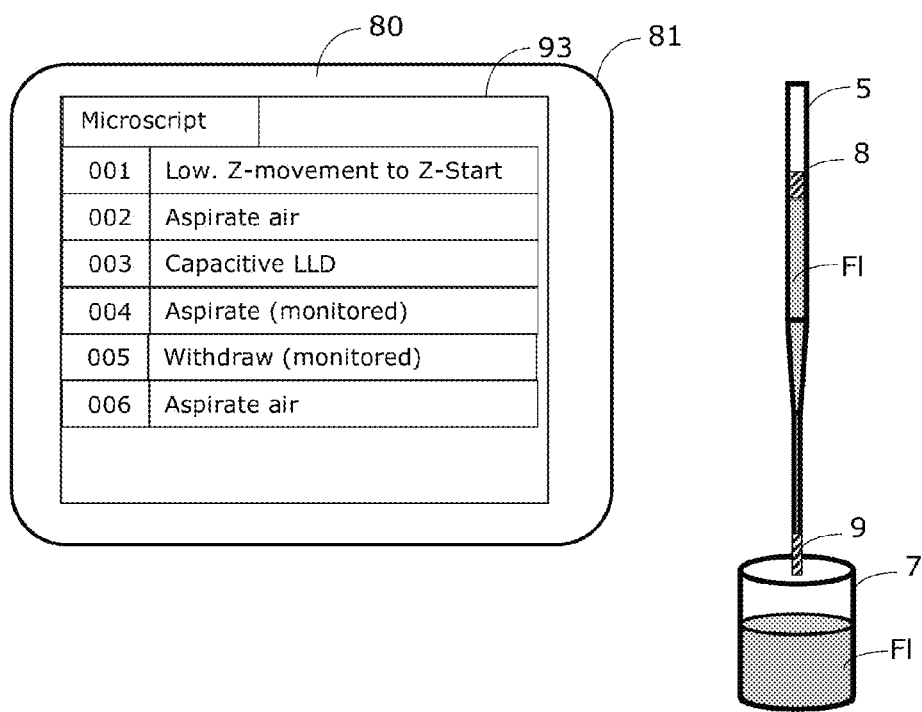
FIG. 11F shows a view of the graphic user interface of FIG. 11A during a sixth aspiration step and the pipette during the aspiration of air.

FIG. 11F shows the graphic user interface 80 during a sixth aspiration step. The pipette 5 aspirates air again in this step. FIG. 11F shows a further small air gap 9 which is situated at the bottom end of the pipette 5. The liquid Fl is now surrounded in the pipette 5 by a leading air gap 8 (LAG) and a trailing air gap 9 (TAG).

Further steps can now follow. The pipette 5 can be brought to a different position for example. Starting from this other position, the substeps of a dispensing process can follow for example. The graphic user interface 80 can also display the individual substeps in this case, too.

The sequence of a pipetting process is rigidly predetermined in current handling systems. The pipette is moved in such a handling system to the height Z-start. The STAG (system trailing air gap) and the LAG (leading air gap) are received jointly by the pipette. The pipette is then subsequently slowly moved in the downward direction with activated LLD monitoring in the direction of the surface of the liquid until the liquid level is detected by the LLD circuit. The pipette is additionally immersed slightly deeper into the liquid. The liquid is then aspirated as a sum total of excess volume, sample volume (Vol.) and conditioning volume (Cond.) at a speed predetermined in the liquid class. The pipette follows the sinking liquid level during the aspiration process. The pipette is then slowly moved out of the liquid again up to Z-start. The TAG (trailing air gap) is then drawn up at Z-start. The sequence of the described steps is rigidly predetermined and cannot be changed. In current systems, at most one of the elements shown in FIG. 12 can be set to zero.

Figure 12:
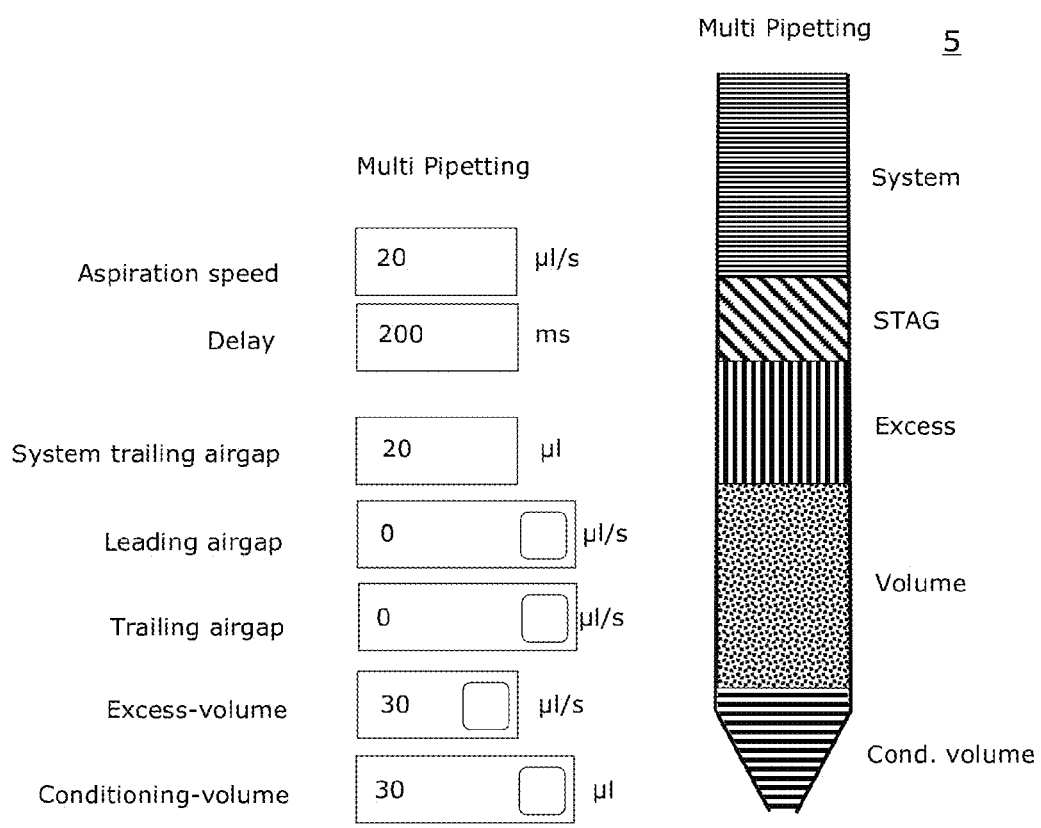
FIG. 12 shows a view of a graphic user interface of a known solution which is provided for defining parameters, and a pipette in a sectional view to the right thereof.

The configuration of the liquid elements and the air gap in a pipette as shown in FIG. 12 on the right-hand side is also predetermined. The volumes of the individual liquid elements and the speeds must be determined in advance and cannot be changed anymore during the pipetting sequence.

However, increasingly higher flexibility is required for modern handling systems. It can be desirable for example to receive several different liquids in a pipette which are separated by air gaps. This is not possible with the rigid liquid class system known from the prior art. In a handling system 100 in accordance with the invention the sequence of individual steps may be adapted by using microscript, and further steps may be defined and inserted. If it is intended to aspirate a liquid which is situated beneath a different liquid layer, the LLD can be activated twice by means of a suitable microscript in order to find the phase boundary of the searched liquid. The aspiration can then be performed there.

It is also possible with the invention to aspirate a first liquid (e.g. a buffer solution) and a second liquid (e.g. the actual sample) and to provide an air gap between the two liquids for example. The invention offers very high flexibility in this case.

LIST OF REFERENCE NUMERALS

Worktable 1
Syringe pump 2
Conduit 3
Plunger 4
Outlet element (e.g. pipette, syringe) 5
Vessel 6
Vessel 7
Air gap 8
Air gap 9
Syringe cylinder 10
Microplate 11
Three-way valve 12
System liquid container 13
Sample retainer 21
Movement apparatus/Handling robot/Drive apparatus 50
Computer 60
Interface 61
Interface 62
Graphic user interface 80
Computer screen 81
Selection structure 82
Action menu 83
Arrow 84
Submenu 85
Submenu 86
Formula submenu 87
Formula field 88
Formula name 89
Unit of measurement 90
Minimum field 91
Maximum field 92
Microscript window 93
Step sequence 94
Graphic symbols (icons) 95
Field 96
Liquid handling system 100
Process 200
Process 201
Process 202
Process 203
Feedback 204
Constant a
Drives A1, A2, A3
Constant b
Constant c
Constant d
Function of x f(x)
Liquid Fl
Hierarchical plane H1, H2, H3
Capacitor K
Asymptotes Pmax, Pmin
Volume at the point of inflection Pmid
Movement P1, P2, P3
Controller S
Control lines s1, s2
Sigmoid function SF
Point of inflection Smax
Steps St1, St2, St3, . . . .
Volume x

The invention claimed is:

1. A method for defining an automated pipetting process which is to be carried out in a liquid handling system (100), wherein the liquid handling system (100) comprises
an outlet element (5) for aspirating and/or dispensing a liquid volume (x) in an automated pipetting process,
a numerically controlled movement apparatus (50) for carrying out movements (P1, P2, P3) in connection with the pipetting process,
a controller (S) for controlling the movement apparatus (50) and the pipetting process,
a graphic user interface (80) for displaying and/or defining parameters for carrying out a pipetting process, and
a set of parameters using which the controller (S) controls a defined pipetting process, wherein parameters of this parameter set are to be defined directly by a user using the graphic user interface (80), characterized in that at least one formula is provided in the graphic user interface (80), said formula being configured to bring at least a first parameter (f(x)), which is to be directly defined by a user, into a functional dependency from a second parameter (x), which is also to be defined directly by a user, so that the first parameter (f(x)) is—instead of being to be defined by a user—adjusted automatically by the system if the second parameter (x) changes, wherein a sigmoid function is used as said formula.

2. A method according to claim 1, characterized in that the graphic user interface (80) is used in order to define substeps of the process, wherein parameters of the parameter set are assigned to the substeps.

3. A method according to claim 2, characterized in that the user is enabled in a process step to bring the substeps into a chronological sequence with respect to each other.

4. A method according to claim 2, characterized in that a computational adjustment between two substeps is carried out in a parallel or temporally subsequent step if said two substeps are dependent on each other.

5. A method according to claim 2, characterized in that the formula is used for carrying out a computational adjustment between two substeps and/or the first parameter (f(x)).

6. A method according to claim 1, characterized in that the graphic user interface (80) allows the user to directly make a basic selection of one or more parameters, preferably a selection of an outlet element (5).

7. A method according to claim 1, characterized in that a formula field (88) is provided in a process step in the region of the graphic user interface (80) in such a way that
  the user can enter the formula in said formula field (88), and/or
  the user is able to select the formula from a collection of formulas and can transfer it in the formula field (88), and/or
  the user can edit the formula which is predetermined by the system in the formula field (88).

8. A method according to claim 7, characterized in that the user is enabled in a process step to enter a minimum value (Pmin) and a maximum value (Pmax) with respect to the formula field (88) and/or the formula.

9. A method according to claim 1, characterized in that the user is enabled in a process step to provide at least one constant (a, b, c, d) to the sigmoid function (SF) for defining the properties of the sigmoid function (SF).

10. A method according to claim 1, characterized in that a computational simulation is carried out in a temporally subsequent step.

11. A method according to claim 1, characterized in that the final parameters are calculated in a temporally subsequent step (St5).

12. A method according to claim 1, characterized in that the set of parameters is provided by a liquid class, said liquid class being selectable by a user and defining a pipetting process for specific liquids.

13. A method according to claim 1, wherein the first parameter f(x) is a pipetting volume or an type of the outlet element, and wherein the second parameter (x) is selected from a group which comprises:
  a trailing air gap,
  a leading air gap,
  an air gap trailing the system liquid,
  am excess volume,
  a conditioning volume,
  a pipetting speed,
  a delay, and
  an accuracy adjustment.

14. A method for carrying out a pipetting process in a liquid handling system (100), which comprises an outlet element (5) for pipetting a liquid volume (x), a numerically controlled movement apparatus (50) for carrying out movements (P1, P2, P3) in connection with the pipetting, a controller (S) for controlling the process steps, and a set of parameters using which the controller (S) controls a defined pipetting process, wherein parameters of this parameter set are assigned to substeps of the pipetting process,
  the method having the following steps:
    providing at least one formula which brings at least one parameter (f(x)) of a substep into a functional dependency from another parameter (x) of another substep,
    using a graphic user interface (80) in order to allow a user to bring substeps of the pipetting process into a chronological sequence with respect to each other;
    using a graphic user interface (80) and the formula in order to allow a user to define a dependence of a first one of the substeps on a second one of substeps in such a way that the first one of the substeps changes when a change has occurred in the second one of the substeps,
  wherein a sigmoid function (SF) is used as a formula.

15. A method according to claim 14, characterized in that in a process step, at least one constant (a, b, c, d) can be specified for the sigmoid function (SF) in order to define the properties of the sigmoid function (SF).

* * * * *